United States Patent
Nuopponen et al.

(10) Patent No.: US 12,359,870 B2
(45) Date of Patent: Jul. 15, 2025

(54) METHOD FOR FREEZE-DRYING A HYDROGEL COMPOSITION AND A FREEZE-DRIED HYDROGEL COMPOSITION

(71) Applicant: UPM-Kymmene Corporation, Helsinki (FI)

(72) Inventors: Markus Nuopponen, Helsinki (FI); Marjo Yliperttula, Espoo (FI); Arto Merivaara, Helsinki (FI); Ossi Korhonen, Hamula (FI); Jacopo Zini, Helsinki (FI); Elle Koivunotko, Helsinki (FI); Lisa Chinello, Padua (IT); Giulia Scapin, Castegnero (IT); Anne Meriluoto, Helsinki (FI); Lauri Paasonen, Järvenpää (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 155 days.

(21) Appl. No.: 17/245,445

(22) Filed: Apr. 30, 2021

(65) Prior Publication Data

US 2022/0349651 A1    Nov. 3, 2022

(51) Int. Cl.
*F26B 5/06* (2006.01)
*C12N 5/00* (2006.01)

(52) U.S. Cl.
CPC .............. *F26B 5/06* (2013.01); *C12N 5/0062* (2013.01); *C12N 2513/00* (2013.01); *C12N 2533/78* (2013.01)

(58) Field of Classification Search
CPC .. C12N 5/0693; C12N 5/0062; C12N 5/0075; C12N 2513/00; C12N 2533/78; C12N 2500/34; B82Y 5/00; B82Y 30/00; B82Y 40/00; A61K 47/38; F26B 5/06
See application file for complete search history.

(56) References Cited

U.S. PATENT DOCUMENTS 11,324,701 B2 *  5/2022  Paukkonen ........... A61L 15/425

FOREIGN PATENT DOCUMENTS

| CN | 110354057 A | * | 10/2019 | |
| EP | 2857583 A1 | | 4/2015 | |
| EP | 3335695 A1 | | 6/2018 | |
| WO | 2018109281 A1 | | 6/2018 | |
| WO | WO-2018108341 A1 | * | 6/2018 | ........... A01N 1/0221 |

OTHER PUBLICATIONS

Nahr et al., LWT-Food Science and Technology 64 (2015) 326-332 Optimization of the nanocellulose based cryoprotective medium to enhance the viability of freeze dried Lactobacillus plantarum using response surface methodology (Year: 2015).*
Morchi et al., Protective Effect of Glutamic Acid and Related Compounds on Bacterial Cells Subjected to Freeze-Drying, J. Gen. Appl. Microbiol. vol. 9, No. 2, 1963 https://doi.org/10.2323/jgam.9.149 (Year: 1963).*
DMEM data sheet from Millipore-Sigma. (https://www.sigmaaldrich.com/US/en/technical-documents/technical-article/cell-culture-and-cell-culture-analysis/mammalian-cell-culture/dulbecco-modified-eagle-medium-formulation) (Year: 2024).*
Extended European Search Report in European Patent Application No. EP 21171449.8, mailed Oct. 18, 2021 (7 pages).
Database WPI Week 201819, Thompson Scientific, London, GB; AN 2018-171577 XP002804407, & CN 107 722 338 A (Univ Tianjin Sci & Technology), Feb. 23, 2018.

* cited by examiner

*Primary Examiner* — Jeremy C Flinders
*Assistant Examiner* — Masudur Rahman
(74) *Attorney, Agent, or Firm* — NIXON PEABODY LLP

(57) ABSTRACT

A method for freeze-drying a hydrogel composition is disclosed, the method comprising providing the hydrogel composition, wherein the hydrogel composition comprises cellulose nanofibrils and/or cellulose nanocrystals, at least one saccharide, at least one amino acid, and biologics; and freeze-drying the hydrogel composition, thereby obtaining a freeze-dried hydrogel composition.

9 Claims, 9 Drawing Sheets

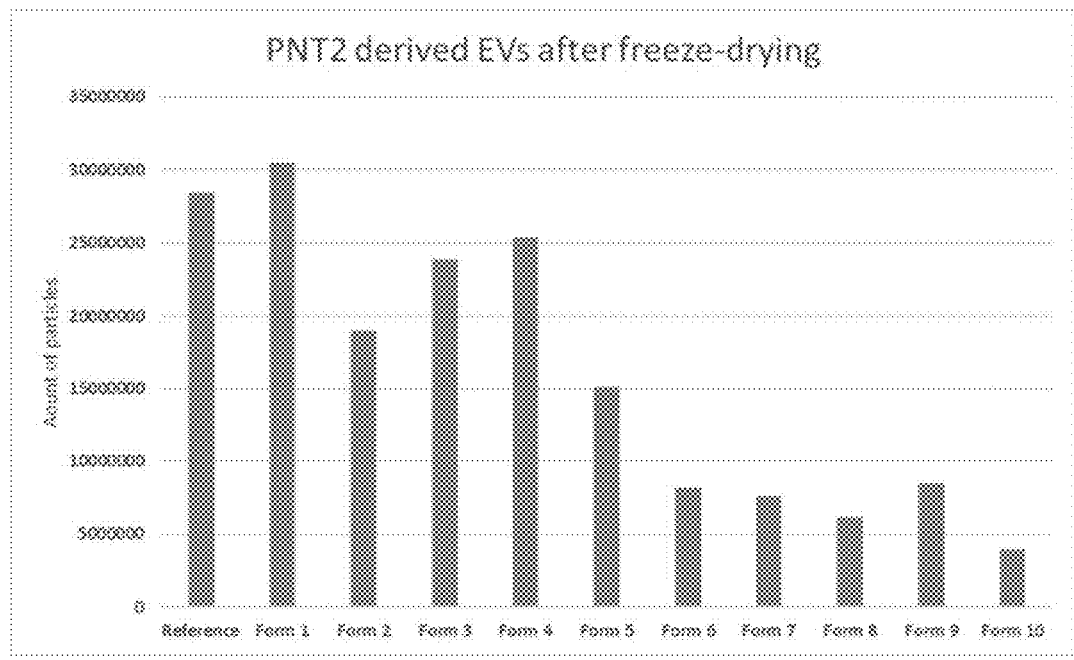
Figure 5
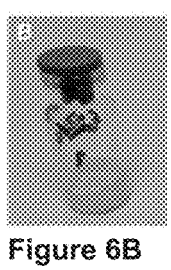
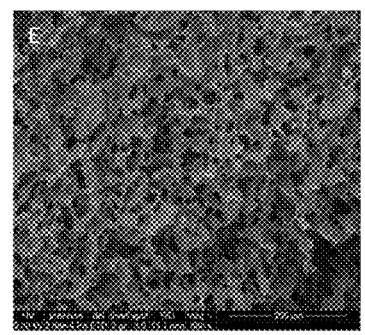
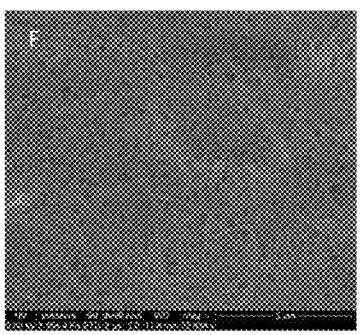
Figure 6A   Figure 6B
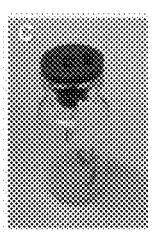
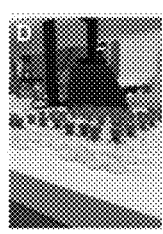
Figure 6E   Figure 6F
Figure 6C   Figure 6D

METHOD FOR FREEZE-DRYING A HYDROGEL COMPOSITION AND A FREEZE-DRIED HYDROGEL COMPOSITION

TECHNICAL FIELD

The present disclosure relates to a method for freeze-drying a hydrogel composition, a freeze-dried hydrogel composition, a method for reconstituting a freeze-dried hydrogel composition, and a reconstituted hydrogel composition.

BACKGROUND

Cellulose nanofibrils and hydrogels obtainable therefrom have unique properties. For example, cells may be cultured in cellulose nanofibril matrices in three-dimensional culture, in which the cells may grow as spheroids.

It may be desirable to be able to dewater and dry cellulose nanofibril hydrogels that contain e.g. cells cultured therein. However, there may be challenges in handling cellulose nanofibrils and hydrogels obtainable therefrom; for example, cellulose nanofibril hydrogel may not be easily dewatered or freeze-dried, and biological material contained in the hydrogel may not survive the process.

SUMMARY

A method for freeze-drying a hydrogel composition is disclosed. The method may comprise providing the hydrogel composition, wherein the hydrogel composition comprises cellulose nanofibrils and/or cellulose nanocrystals, at least one saccharide, at least one amino acid, and biologics; and freeze-drying the hydrogel composition, thereby obtaining a freeze-dried hydrogel composition.

A freeze-dried hydrogel composition comprising cellulose nanofibrils and/or nanocrystals, at least one saccharide, at least one amino acid, and biologics, is disclosed. The residual water content of the freeze-dried hydrogel composition may be at most 5 w-%.

A method for reconstituting a freeze-dried hydrogel composition is disclosed. The method may comprise adding water or an aqueous solution to the freeze-dried hydrogel composition according to one or more embodiments described in this specification.

A reconstituted hydrogel composition comprising nanofibrils and/or nanocrystals, at least one saccharide, at least one amino acid, and biologics, is disclosed.

BRIEF DESCRIPTION OF THE DRAWINGS

The accompanying drawings, which are included to provide a further understanding of the embodiments and constitute a part of this specification, illustrate various embodiments. In the drawings:

FIG. 5 shows the amount of the PNT2 cell line derived EVs after the FDing in the nNFC formulations and reconstitution and the enzymatic degradation of nNFC, and the FDing of those EVs without nNFC hydrogel formulations.

FIG. 6A shows white, solid cakes of FDed NFC with trehalose.

FIG. 6B shows white, solid cakes of FDed NEC with trehalose and glycine.

FIG. 6C shows white, solid cakes of FDed NFC with trehalose, glycine and DMSO.

FIG. 6D shows white, solid cakes of FDed NEC; overall image.

FIG. 6E shows a SEM micrograph showing the porous aerogel structure of NFC when trehalose is used as excipient.

FIG. 6F shows a SEM micrograph showing the nanofibers in ordered structure when trehalose is used as excipient.

DETAILED DESCRIPTION

Figure 1:
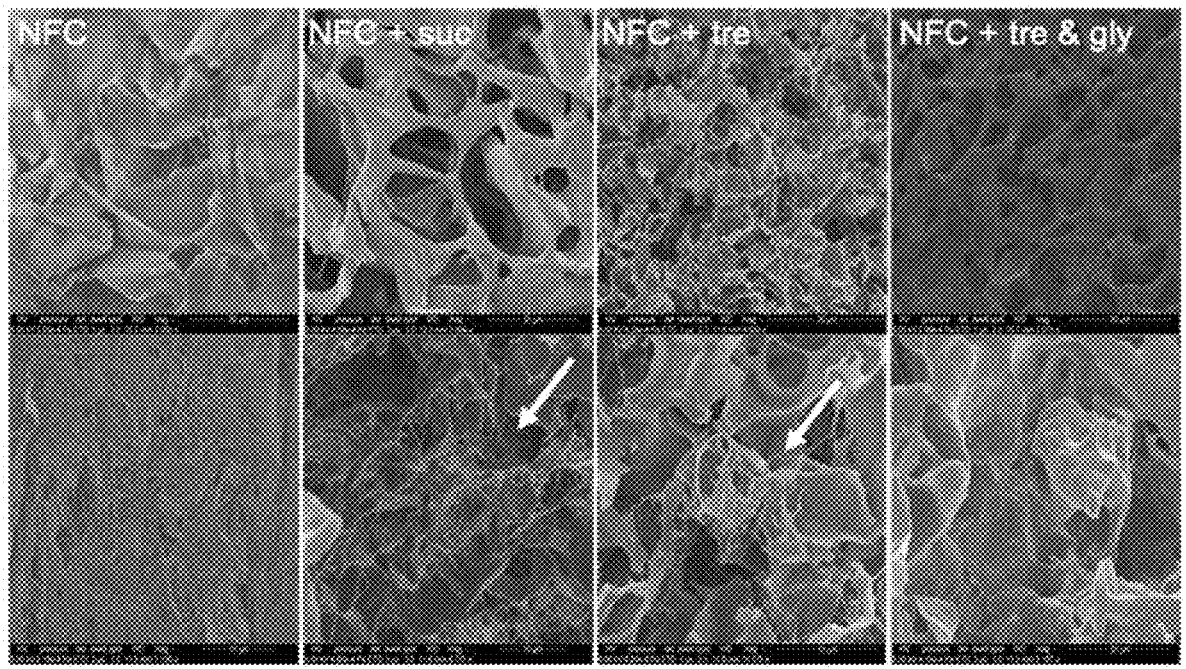
FIG. 1 shows SEM images of freeze-dried NFC formulation without the excipients (left), with 300 mM of sucrose (left-middle), 300 mM of trehalose (right-middle), 150 mM of trehalose and 333 mM of glycine (right). Zoomed images of the same formulation is presented underneath. Arrows indicate an example of the individual fibrous ribbon observed in the formulations including only trehalose or sucrose. Abbreviations: suc=sucrose, tre=trehalose, gly=glycine.

A method for freeze-drying a hydrogel composition is disclosed. The method may comprise providing the hydrogel composition, wherein the hydrogel composition comprises cellulose nanofibrils and/or cellulose nanocrystals, at least one saccharide, at least one amino acid, and biologics; and freeze-drying the hydrogel composition, thereby obtaining a freeze-dried hydrogel composition.

A freeze-dried hydrogel composition is also disclosed. The freeze-dried hydrogel composition may comprise cellulose nanofibrils and/or cellulose nanocrystals, at least one saccharide, at least one amino acid, and biologics. The residual water content of the hydrogel composition may be at most 5 wt-%.

A method for reconstituting a freeze-dried hydrogel composition, the method comprising adding water or an aqueous solution to the freeze-dried hydrogel composition according to one or more embodiments described in this specification. A reconstituted hydrogel composition may thus be obtained.

A reconstituted hydrogel composition is also disclosed. The reconstituted hydrogel may comprise nanofibrils and/or nanocrystals, at least one saccharide, at least one amino acid, and biologics. The reconstituted hydrogel composition may obtainable by the method for reconstituting a freeze-dried hydrogel composition according to one or more embodiments described in this specification.

With the method for freeze-drying, it may be possible to successfully dry and subsequently reconstitute a hydrogel composition and the biologics included therein. A low residual water content may be achieved, and a regular fibre matrix structure of the hydrogel composition may be obtained. The formation of ice crystals during the freeze-drying may be reduced or even obviated. Further, the biologics included in the hydrogel composition may be well preserved during the freeze-drying and the reconstitution. For example, lipid structures, such as cell membranes, membranes of exosomes, or other lipid bilayers may remain stable during the freeze-drying and the reconstitution. As a further example, the cytoskeleton of cells may remain intact during the freeze-drying and the reconstitution, at least partially. As cell membranes and the cytoskeleton are not damaged, cells may remain viable and may proliferate.

The freeze-dried hydrogel composition may e.g. be suitable for stable long-term storage and/or transport. The freeze-dried hydrogel composition may e.g. be suitable for storage in room temperature.

Not to be bound by theory, it may be that the at least one saccharide may concentrate at the interface of water and cellulose nanofibrils and/or cellulose nanocrystals, thereby assisting in preserving the structure of the hydrogel during and after freeze-drying. The at least one amino acid may increase the binding of the at least one saccharide to the cellulose nanofibrils and/or cellulose nanocrystals. The at least one saccharide and the at least one amino acid may thus synergistically function as lyoprotectants for the hydrogel structure and possibly to the biologics contained therein.

The hydrogel composition comprising cellulose nanofibrils may be referred to as a nanofibrillar cellulose hydrogel.

In the context of this specification, the term "reconstitute" or "reconstitution" may be understood as referring to adding water and/or an aqueous solution to a freeze-dried hydrogel composition, such that the (residual) water content of the freeze-dried hydrogel composition is increased or returned to its original state prior to the freeze-drying. Upon reconstitution, the freeze-dried hydrogel composition, e.g. an aerogel, may (again) form a hydrogel.

In the context of this specification, the term "cellulose nanofibrils" may be understood as referring to nanofibrillar cellulose. These terms may be used interchangeably.

The cellulose nanofibrils and/or cellulose nanocrystals may be prepared from cellulose raw material of plant origin. The raw material may be based on any plant material that contains cellulose. The raw material may also be derived from certain bacterial fermentation processes. In an embodiment, the plant material is wood. Wood may be from a softwood tree, such as spruce, pine, fir, larch, douglas-fir or hemlock, or from a hardwood tree, such as birch, aspen, poplar, alder, eucalyptus, oak, beech or acacia, or from a mixture of softwoods and hardwoods. In an embodiment, the cellulose nanofibrils and/or cellulose nanocrystals is/are obtained from wood pulp. In an embodiment, the cellulose nanofibrils and/or cellulose nanocrystals is/are obtained from hardwood pulp. In an example, the hardwood is birch. In an embodiment, the cellulose nanofibrils and/or cellulose nanocrystals is/are obtained from softwood pulp.

The cellulose nanofibrils and/or cellulose nanocrystals may be made of plant material. In an example, the cellulose nanofibrils and/or cellulose nanocrystals are obtained from non-parenchymal plant material. In such a case, the cellulose nanofibrils and/or cellulose nanocrystals may be obtained from secondary cell walls. One abundant source of such cellulose fibrils is wood fibres. The smallest cellulosic entities of cellulose pulp of plant origin, such as wood, include cellulose molecules, elementary fibrils, and microfibrils. Microfibril units are bundles of elementary fibrils caused by physically conditioned coalescence as a mechanism of reducing the free energy of the surfaces.

The cellulose nanofibrils may be manufactured by homogenizing wood-derived fibrous raw material, which may be chemical pulp. Cellulose fibers may be mechanically disintegrated to produce fibrils which have a diameter in the nanometer range, which diameter may be up to 200 nm, or up to 50 nm, for example in the range of 1-200 nm or 1-100 nm, and gives a dispersion of fibrils in water. The cellulose nanofibrils may be type I cellulose. The fibrils may be reduced to a size in which the diameter of most of the fibrils is in the range of 2-20 nm. The fibrils originating from secondary cell walls may be essentially crystalline, with a degree of crystallinity of at least 55%. Such fibrils may have different properties than fibrils originated from primary cell walls; for example, the dewatering of fibrils originating from secondary cell walls may be more challenging.

In the context of this specification, the term "cellulose nanofibrils" may refer to cellulose fibrils or fibril bundles separated from cellulose-based fiber raw material. These fibrils are characterized by a high aspect ratio (length/diameter): their length may exceed 1 μm, whereas the diameter typically remains smaller than 200 nm. The smallest fibrils are in the scale of so-called elementary fibrils, their diameter being typically in the range of 2-12 nm. The dimensions and size distribution of the fibrils may depend on the refining method and efficiency. Cellulose nanofibrils may be characterized as a cellulose-based material, in which the median length of particles (fibrils or fibril bundles) is not greater than 50 μm, for example in the range of 1-50 μm, and the particle diameter is smaller than 1 μm, for example in the range of 2-500 nm. In case of native cellulose nanofibrils, in an embodiment the average diameter of a fibril is in the range of 5-100 nm, for example in the range of 10-50 nm. Intact, unfibrillated microfibril units may be present in the nanofibrils or the hydrogel composition. In the context of this specification, the term "cellulose nanofibrils" is not meant to encompass non-fibrillar, rod-shaped cellulose nanocrystals or whiskers.

The term "cellulose nanocrystals" may be understood, in the context of this specification, to refer to non-fibrillar, rod-shaped cellulose nanocrystals. Cellulose nanocrystals are a highly crystalline material; it may be referred to as cellulose nanocrystals (CNC), nanocrystals of cellulose (NCC) or cellulose nanowhiskers (CNW). The nanocrystals are rod-like and stiff, have a narrow size distribution and are shorter than nanofibrils. The nanocrystals also have lower viscosity and yield strength and are typically not as good at holding water as nanofibrillar cellulose. The cellulose nanocrystals may have a width of about 2-30 nm. The cellulose nanocrystals may have a length of about 100 nm to several micrometers, or e.g. 100-250 nm. They may be obtainable or obtained by acid hydrolysis of cellulose fibers, whereby non-crystalline regions of the cellulose fibers may be selectively degraded. In the early stage of the hydrolysis, the acid may diffuse into the non-crystalline parts of the cellulose fibers and hydrolyze the glycosidic bonds. After these, more easily accessible glycosidic bonds in the cellulose fibers may be hydrolyzed. Finally hydrolysis may occur at the reducing end groups and at the surface of the nanocrystals.

The nomenclature relating to cellulose nanofibrils is currently not uniform, and terms may be inconsistently used in the literature. For example, the following terms may have been used as synonyms for cellulose nanofibrils and/or for nanofibrillar cellulose: cellulose nanofiber (CNF), nanofibril cellulose, nanofibrillated cellulose (NFC), nanocellulose, nano-scale fibrillated cellulose, microfibrillar cellulose, cellulose microfibrils, microfibrillated cellulose (MFC), and fibril cellulose.

Thus a hydrogel comprising cellulose nanofibrils may refer to a nanofibrillar cellulose (NFC) hydrogel e.g. in this specification.

Cellulose nanofibrils are characterized by a large specific surface area and a strong ability to form hydrogen bonds. In water dispersion, the cellulose nanofibrils typically appear as either light or turbid gel-like material. Depending on the fiber raw material, cellulose nanofibrils may also contain small amounts of other wood components, such as hemicellulose or lignin. The amount is dependent on the plant source.

Different grades of cellulose nanofibrils may be categorized based on three main properties: (i) size distribution, length and diameter; (ii) chemical composition; and (iii) rheological properties. To fully describe a grade, the properties may be used in parallel. Examples of different grades may include native (or non-modified) cellulose nanofibrils, oxidized cellulose nanofibrils (high viscosity), oxidized cellulose nanofibrils (low viscosity), and carboxymethylated cellulose nanofibrils. Within these main grades, also subgrades may exist, for example: extremely well fibrillated vs. moderately fibrillated, high degree of substitution vs. low, low viscosity vs. high viscosity, etc. The fibrillation technique and the chemical pre-modification may have an influence on the fibril size distribution. Typically, non-ionic grades may have a wider fibril diameter (for example in the range of 10-100 nm, or 10-50 nm), while the chemically modified grades may be thinner (for example in the range of 2-20 nm). The distributions of the fibril dimensions may be also narrower for the modified grades. Certain modifications, especially TEMPO oxidation, may yield shorter fibrils.

Depending on the raw material source, e.g. hardwood (HW) vs. softwood (SW) pulp, different polysaccharide compositions may be present in the final nanofibrillar product. Commonly, the non-ionic grades are prepared from bleached birch pulp, which may yield a high xylene content (25% by weight). Modified grades may be prepared either from HW or SW pulps. In such modified grades, the hemicelluloses may also be modified together with the cellulose domain. The modification may not be homogeneous, i.e. some parts may be modified to a greater extent than others. Thus, a detailed chemical analysis may not be possible—the modified products are typically complex mixtures of different polysaccharide structures.

In an aqueous environment, a dispersion of cellulose nanofibrils may form a viscoelastic hydrogel network. The gel may be formed at relatively low concentrations of, for example, 0.05-0.2% (w/w), dispersed and hydrated entangled fibrils. The viscoelasticity of the NFC hydrogel may be characterized, for example, by dynamic oscillatory rheological measurements. The cellulose nanofibril hydrogels may exhibit characteristic rheological properties. For example, they are shear-thinning or pseudoplastic materials, which means that their viscosity depends on the speed (or force) by which the material is deformed. When measuring the viscosity in a rotational rheometer, the shear-thinning behavior is seen as a decrease in viscosity with increasing shear rate. The hydrogels show plastic behavior, which means that a certain shear stress (force) is required before the material starts to flow readily. This critical shear stress is often called the yield stress. The yield stress can be determined from a steady state flow curve measured with a stress-controlled rheometer. When the viscosity is plotted as function of applied shear stress, a dramatic decrease in viscosity can be seen after exceeding the critical shear stress. The zero-shear viscosity and the yield stress may be the most important rheological parameters to describe the suspending power of the materials. These two parameters may separate the different grades quite clearly and thus may enable classification of the grades.

The dimensions of the fibrils or fibril bundles may be dependent on the raw material and the disintegration method. Mechanical disintegration of the cellulose raw material may be carried out with any suitable equipment such as a refiner, grinder, disperser, homogenizer, colloider, friction grinder, pin mill, rotor-rotor dispergator, ultrasound sonicator, fluidizer such as microfluidizer, macrofluidizer or fluidizer-type homogenizer. The disintegration treatment may be performed at conditions in which water is sufficiently present to prevent the formation of bonds between the fibers.

In an example, the disintegration is carried out by using a disperser having at least one rotor, blade or similar moving mechanical member, such as a rotor-rotor dispergator. One example of a rotor-rotor dispergator is an Atrex device.

Another example of a device suitable for disintegrating is a pin mill, such as a multi-peripheral pin mill. One example of such device is described in U.S. Pat. No. 6,202,946 B1.

In an embodiment, the disintegrating is carried out by using a homogenizer.

In the context of this specification, the term "fibrillation" may generally refer to disintegrating fiber material mechanically by work applied to the particles, whereby cellulose fibrils are detached from the fibers or fiber fragments. The work may be based on various effects, such as grinding, crushing or shearing, or a combination of these, or another corresponding action that reduces the particle size. The energy taken by the refining work may normally be expressed in terms of energy per processed raw material quantity, in units of e.g. kWh/kg, MWh/ton, or units proportional to these. The expressions "disintegration" or "disintegration treatment" may be used interchangeably with "fibrillation". The fiber material dispersion that is subjected to fibrillation may be a mixture of fiber material and water (or an aqueous solution), also herein called "pulp". The fiber material dispersion may refer generally to whole fibers, parts (fragments) separated from them, fibril bundles, or fibrils mixed with water, and typically the aqueous fiber material dispersion is a mixture of such elements, in which the ratios between the components are dependent on the degree of processing or on the treatment stage, for example number of runs or "passes" through the treatment of the same batch of fiber material.

The disintegrated fibrous cellulosic raw material may be modified or nonmodified fibrous raw material. Modified fibrous raw material means raw material where the fibers are affected by a modification treatment so that cellulose nanofibrils are more easily detachable from the fibers. The modification may be performed to fibrous cellulosic raw material which exists as a suspension in a liquid, e.g. pulp.

The modification treatment to the fibers may be chemical or physical. In chemical modification, the chemical structure of cellulose molecule is changed by a chemical reaction ("derivatization" of cellulose), for example so that the length of the cellulose molecule is not affected but functional groups are added to 3-D-glucopyranose units of the polymer. The chemical modification of cellulose may take place at a certain conversion degree, which is dependent on the dosage of reactants and the reaction conditions, and often it is not complete so that the cellulose will stay in solid form as fibrils and does not dissolve in water. In physical modification anionic, cationic, or nonionic substances or any combination of these may be physically adsorbed on cellulose surface. The modification treatment may also be enzymatic. The cellulose in the fibers may be particularly ionically charged after the modification, because the ionic charge of the cellulose may weaken the internal bonds of the fibers and may later facilitate the disintegration to cellulose nanofibrils. The ionic charge may be achieved by chemical or physical modification of the cellulose. The fibers may have a higher anionic or cationic charge after the modification compared with the starting raw material. Commonly used chemical modification methods for making an anionic charge may include oxidation, where hydroxyl groups are oxidized to aldehydes and carboxyl groups, sulphonization and carboxymethylation. A cationic charge in turn may be created chemically by cationization by attaching a cationic group to the cellulose, such as a quaternary ammonium group.

The cellulose may be oxidized. In the oxidation of cellulose, primary hydroxyl groups of cellulose may be oxidized catalytically by a heterocyclic nitroxyl compound, for example 2,2,6,6-tetramethylpiperidinyl-1-oxy free radical, generally called "TEMPO". At least some of the primary hydroxyl groups (C6-hydroxyl groups) of the cellulosic β-D-glucopyranose units may be selectively oxidized to carboxylic groups. Some aldehyde groups may also be formed from the primary hydroxyl groups. The cellulose may be oxidized to a level having a carboxylic acid content in the oxidized cellulose in the range of 0.6-1.4 mmol COOH/g pulp, or 0.8-1.2 mmol COOH/g pulp, for example to 1.0-1.2 mmol COOH/g pulp, determined by conductometric titration. When the fibers of oxidized cellulose obtained in this manner are disintegrated in water, they may give a stable transparent dispersion of individualized cellulose fibrils, which may be, for example, of 3-5 nm in width.

The cellulose nanofibrils may also be characterized by the average diameter (or width), or by the average diameter together with the viscosity, such as Brookfield viscosity or zero shear viscosity. In an embodiment, said cellulose nanofibrils have a number average diameter of a fibril in the range of 1-100 nm. In an embodiment, the cellulose nanofibrils have a number average diameter of fibrils in the range of 1-50 nm. In an embodiment, the cellulose nanofibrils have a number average diameter of fibrils in the range of 2-15 nm, such as TEMPO oxidized nanofibrillar cellulose. The diameter of a fibril or fibrils may be determined using several techniques, such as by microscopy. Fibril thickness and width distribution may be measured by image analysis of the images from a field emission scanning electron microscope (FE-SEM), a transmission electron microscope (TEM), such as a cryogenic transmission electron microscope (cryo-TEM), or an atomic force microscope (AFM). In general, AFM and TEM may be well suited for cellulose nanofibril grades with narrow fibril diameter distribution.

The viscosity of the cellulose nanofibrils or of the hydrogel composition may be measured using a rheometer. In an example, a rheometer viscosity of the nanofibrillar cellulose dispersion is measured at 22° C. with a stress controlled rotational rheometer (AR-G2, TA Instruments, UK) equipped with a narrow gap vane geometry (the vane having a diameter of 28 mm and a length of 42 mm) in a cylindrical sample cup having a diameter of 30 mm. After loading the samples to the rheometer they are allowed to rest for 5 min before the measurement is started. The steady state viscosity is measured with a gradually increasing shear stress (proportional to applied torque) and the shear rate (proportional to angular velocity) is measured. The reported viscosity (=shear stress/shear rate) at a certain shear stress is recorded after reaching a constant shear rate or after a maximum time of 2 min. The measurement is stopped when a shear rate of 1000 s-1 is exceeded. This method may be used for determining the zero-shear viscosity.

In one example, the cellulose nanofibrils, when dispersed in water, provide a zero shear viscosity ("plateau" of constant viscosity at small shearing stresses) in the range of 1000-100000 Pa·s, such as in the range of 5000-50000 Pa·s, and a yield stress (shear stress where the shear thinning begins) in the range of 1-50 Pa, such as in the range of 3-15 Pa, determined by rotational rheometer at a consistency of 0.5% (w/w) by weight in aqueous medium.

The cellulose nanofibrils may have a storage modulus in the range of 0.3 to 50 Pa, when dispersed to a concentration of 0.5 w % in water. For example, the storage modulus may be in the range of 1 to 20 Pa, or in the range of 2 to 10 Pa, when dispersed to a concentration of 0.5 w % in water.

Turbidity is the cloudiness or haziness of a fluid caused by individual particles (total suspended or dissolved solids) that are generally invisible to the naked eye. There are several practical ways of measuring turbidity, the most direct being some measure of attenuation (that is, reduction in strength) of light as it passes through a sample column of water. The alternatively used Jackson Candle method (units: Jackson Turbidity Unit or JTU) is essentially the inverse measure of the length of a column of water needed to completely obscure a candle flame viewed through it.

Turbidity may be measured quantitatively using optical turbidity measuring instruments. There are several commercial turbidometers available for measuring turbidity quantitatively. In the present case the method based on nephelometry is used. The units of turbidity from a calibrated nephelometer are called Nephelometric Turbidity Units (NTU). The measuring apparatus (turbidometer) is calibrated and controlled with standard calibration samples, followed by measuring of the turbidity of the diluted NFC sample. In a turbidity measurement method, a nanofibrillar cellulose sample may be diluted in water, to a concentration below the gel point of said nanofibrillar cellulose, and turbidity of the diluted sample may be measured. The concentration in which the turbidity of the cellulose nanofibril samples is measured may be 0.1%. HACH P2100 Turbidometer with a 50 ml measuring vessel may be used for turbidity measurements. The dry matter of the cellulose nanofibril sample is determined and 0.5 g of the sample, calculated as dry matter, may be loaded in the measuring vessel, which may be filled with tap water to 500 g and vigorously mixed by shaking for about 30 s. Without delay the aqueous mixture may be divided into 5 measuring vessels, which are inserted in the turbidometer. Three measurements on each vessel may be carried out. The mean value and standard deviation may be calculated from the obtained results, and the final result may be given as NTU units.

One way to characterize cellulose nanofibrils or a hydrogel comprising them is to define both the viscosity and the turbidity. Low turbidity may correlate with a small size of the fibrils, such as small diameter, as small fibrils scatter light poorly. In general as the fibrillation degree increases, the viscosity increases and at the same time the turbidity decreases. This may happen, however, until a certain point. When the fibrillation is further continued, the fibrils may finally begin to break and cannot form a strong network any more. Therefore, after this point, both the turbidity and the viscosity may begin to decrease.

In an example, the turbidity of anionic cellulose nanofibrils or of a hydrogel comprising them is lower than 90 NTU, for example from 3 to 90 NTU, such as from 5 to 60, for example 8-40, measured at a consistency of 0.1% (w/w) in aqueous medium, and measured by nephelometry. In an example the turbidity of native cellulose nanofibrils or of a hydrogel comprising them may be even over 200 NTU, for example from 10 to 220 NTU, such as from 20 to 200, for example 50-200 measured at a consistency of 0.1% (w/w) in aqueous medium, and measured by nephelometry. To characterize the cellulose nanofibrils or a hydrogel comprising them, these ranges may be combined with the viscosity ranges of the cellulose nanofibrils or of a hydrogel comprising them.

The hydrogel composition may be provided e.g. by mixing a hydrogel comprising the cellulose nanofibrils and/or cellulose nanocrystals with a solution comprising the at least one saccharide and the at least one amino acid. The biologics may be mixed with the hydrogel and the solution, or the biologics may e.g. be contained in the hydrogel (for example, as a result of culturing them within the hydrogel).

The hydrogel composition (i.e. the hydrogel composition prior to the freeze-drying) may comprise cell culture medium. The method may further comprise removing the cell culture medium from the hydrogel composition at least partially and replacing it with a solution comprising the at least one saccharide and the at least one amino acid prior to freeze-drying the hydrogel composition.

The content or concentration of the at least one saccharide in the hydrogel composition (prior to the freeze-drying) may be in the range of 100-1000 mM. It may, alternatively or additionally, be in the range of 150-500 mM. In embodiments in which the at least one saccharide comprises two or more saccharides, the total (i.e. combined) content or concentration of the two or more saccharides may be in the range of 100-1000 mM, or 150-500 mM.

The content or concentration of the at least one amino acid in the hydrogel composition (prior to the freeze-drying) may be in the range of 50-700 mM. It may, alternatively or additionally, be in the range of 100-500 mM. In embodiments in which the at least one amino acid comprises two or more amino acids, the total (i.e. combined) content or concentration of the two or more amino acids may be in the range of 50-700 mM, or 100-500 mM.

The concentration (consistency) of the hydrogel composition may be e.g. up to 2 wt-%, or up to 1 wt-%, or 0.2-2 wt-%.

The cellulose nanofibrils may comprise or be native, i.e. unmodified, cellulose nanofibrils.

In an embodiment, the cellulose nanofibrils comprise chemically modified cellulose nanofibrils, such as anionically modified cellulose nanofibrils. In an embodiment, the cellulose nanofibrils are anionically modified cellulose nanofibrils. In an embodiment, the anionically modified cellulose nanofibrils are oxidized cellulose nanofibrils. In an embodiment, the anionically modified cellulose nanofibrils are sulphonized cellulose nanofibrils. In an embodiment, the anionically modified cellulose nanofibrils are carboxymethylated cellulose nanofibrils.

Freeze-drying is a preservation method which is suitable for drying of e.g. heat sensitive biological products. It is widely used in preservation of protein pharmaceuticals, vaccines and other biologics. In the freeze-drying process, the hydrogel composition may be first frozen below its glass transition (Tg') temperature in a freeze-drying chamber; this may be referred to as the freezing phase. Then the pressure in the freeze-drying chamber may be decreased under the triple point of water; this may be referred to as the primary drying phase. The primary drying may result in sublimation of the frozen water contained in the hydrogel composition. After the primary drying, the hydrogel composition may be heated, and the temperature may be slowly increased to further sublimate the unfrozen bound water; this may be referred to as the secondary drying phase. In other words, the freeze-drying may comprise freezing the hydrogel composition, a primary drying phase and a secondary drying phase. The product of this process may be a dry solid formulation which can be stored in room temperature or in refrigerator and reconstituted by adding water or a suitable aqueous solution.

For example, the hydrogel composition may be frozen by decreasing the temperature in which the hydrogel composition is held by 0.5-2° C./minute until it reaches a temperature below its glass transition temperature; in the primary drying phase, the pressure may be decreased to about 30-100 mTorr and the temperature increased to about −40 to −60° C.; and in the secondary drying phase, the temperature in which the hydrogel composition is held is increased by 0.5-2° C./minute until it reaches room temperature (e.g., about 20-25° C.).

As a further example, the hydrogel composition may be frozen by decreasing the temperature in which the hydrogel composition is held by 1° C./minute until it reaches about −55° C.; in the primary drying phase, the pressure may be decreased to about 100 mTorr and the temperature increased to about −40 to −50° C.; and in the secondary drying phase, the temperature in which the hydrogel composition is held is increased by 1° C./minute until it reaches room temperature (e.g., about 20-25° C.).

The freeze-drying may be performed with monitoring of the residual water content and/or by controlling the decrease in temperature with a thermal gradient, such that the temperature of the hydrogel composition is maintained below the collapsing temperature of the hydrogel composition. Freeze-drying at a temperature higher than the collapsing temperature may lead to collapse of the hydrogel composition; while freeze-drying at a lower temperature may lead to a longer, and thereby more expensive, freeze-drying cycle.

The glass transition temperature of the hydrogel composition may be measured prior to the freeze-drying and the freeze-drying cycle may be adjusted based on the measured glass transition temperature. The temperature of the hydrogel composition may then be maintained below the glass transition temperature of the hydrogel composition.

As the residual water content of the freeze-dried hydrogel composition may be relatively low, the freeze-dried hydrogel composition may be considered, at least in some embodiments, to be an aerogel or aerogel composition.

The residual water content of the freeze-dried hydrogel composition may be e.g. at most 4 w-%, or at most 2 wt-%, or at most 1 wt-%, or 0.2-3 wt-%, or 0.5-2 wt-%. The residual water content may include the residual water content of the biologics in the freeze-dried hydrogel composition. In other words, the residual water content of the freeze-dried hydrogel composition may be the total residual water content of all components of the freeze-dried hydrogel composition. The residual water content may thus depend e.g. on the (relative) amount of the biologics in the freeze-dried hydrogel composition and/or the nature of the biologics. For example, cells may contain a higher residual water content as compared e.g. to the hydrogel portion of the freeze-dried hydrogel composition. The residual water content may also depend e.g. on the content of the at least one saccharide and/or of the content of the at least one amino acid in the freeze-dried hydrogel composition.

The residual water content may be understood as referring to the amount of water, for example water bound to the freeze-dried hydrogel composition, which remains in the freeze-dried hydrogel composition during and/or after the secondary drying phase of the freeze-drying. The residual water content may be determined by titration, e.g. as described in the Examples. As water is being removed during freeze-drying, an amount of residual water may be important for the reconstitution of the freeze-dried hydrogel composition; however, water should preferably not be present at such high amounts that it would damage the biologics by the formation of ice crystals.

The freeze-dried hydrogel composition may be a freeze-dried aerogel or a freeze-dried aerogel composition.

The at least one amino acid may comprise or be any suitable amino acid, for example a naturally occurring and/or a proteinogenic amino acid. The at least one amino acid may comprise or be one or more of the following amino acids: glycine, arginine, histidine, lysine, aspartic acid, glutamic acid, serine, threonine, asparagine, glutamine, cysteine, selenocysteine, proline, alanine, isoleucine, leucine, methionine, phenylalanine, tryptophan, tyrosine, valine, or a mixture or combination thereof.

The at least one amino acid may comprise or be one or more of the following amino acids with positively charged side chains: arginine, histidine, lysine, and/or a mixture or combination thereof.

The at least one amino acid may comprise or be one or more of the following amino acids with negatively charged side chains: aspartic acid, glutamic acid, and/or a mixture or combination thereof.

The at least one amino acid may comprise or be one or more of the following amino acids with uncharged side chains: serine, threonine, asparagine, glutamine, and/or a mixture or combination thereof.

The at least one amino acid may comprise or be one or more of the following amino acids: glycine, cysteine, selenocysteine, proline, and/or a mixture or combination thereof.

The at least one amino acid may comprise or be one or more of the following amino acids with hydrophobic side chains: alanine, isoleucine, leucine, methionine, phenylalanine, tryptophan, tyrosine, valine, and/or a mixture or combination thereof.

Any amino acid described in this specification may be an L-stereoisomer of said amino acid.

The at least one amino acid may comprise or be glycine, leucine, isoleucine, alanine, tryptophan, asparagine glutamine, and/or a mixture or combination thereof.

The at least one amino acid may comprise or be glycine.

The at least one amino acid may comprise or be tryptophan, asparagine, glutamine, and/or a mixture or combination thereof.

The at least one saccharide may comprise or be at least one of a disaccharide, a trisaccharide, an oligosaccharide, or a mixture or combination thereof.

The at least one saccharide may comprise or be at least one of a disaccharide, a trisaccharide, or a mixture or combination thereof.

In the context of this specification, the term "oligosaccharide" may be understood, at least in some embodiments, to refer to a saccharide comprising 3-10, or 3-6 monosaccharide units (residues).

Examples of disaccharides may include e.g. lactose, maltose, sucrose, cellobiose, trehalose, melibiose, and gentiobiose.

The at least one saccharide may comprise or be at least one of sucrose, trehalose, lactose, fructose, glucose, or a mixture or combination thereof.

The at least one saccharide may comprise or be at least one of sucrose, trehalose, lactose, or a mixture or combination thereof.

The at least one saccharide may be or comprise at least one non-reducing saccharide. However, reducing saccharides may also be contemplated.

The content of the at least one saccharide in the freeze-dried hydrogel composition may be in the range of 15-80 mol %, or 30-70 mol %.

The content of the at least one amino acid in the freeze-dried hydrogel composition may be in the range of 15-60 mol %.

The mole percentage (mol %) of the at least one saccharide and/or of the at least one amino acid in the freeze-dried hydrogel composition may be understood as their mole percentage relative to all molecules (including water) in the freeze-dried hydrogel composition, i.e. as the amount of the at least one saccharide and/or of the at least one amino acid (in moles) divided by the total amount of all constituents (molecules) in the freeze-dried hydrogel composition (in moles).

The mole percentage (mol %) of the at least one saccharide and/or of the at least one amino acid in the freeze-dried hydrogel composition may depend e.g. on the mol % of the cellulose nanofibrils and/or cellulose nanocrystals in the freeze-dried hydrogel composition.

The ratio of the content of the at least one saccharide and the content of the at least one amino acid may be in the range of 10:1-1:5 in the freeze-dried hydrogel composition and/or in the hydrogel composition. Additionally or alternatively, the ratio of the content of the at least one saccharide and the content of the at least one amino acid may be in the range of 6:1-1:4.

Various physicochemical properties of the hydrogel composition, such as pH, osmolarity, and/or ionic strength may be controlled prior to the freeze-drying. For example, the osmolarity of the hydrogel composition may be adjusted or controlled to provide an osmolarity of the hydrogel composition that is suitable for reconstitution, e.g. to enhance the stability of lipid structures, or to otherwise optimize the properties of the freeze-dried hydrogel composition. For example, HEPES, other suitable buffering agent, or other suitable component may be included in the hydrogel composition at a concentration such that the osmolarity of the hydrogel composition is suitable for reconstitution. Thus breakage of lipid structures, such as cell membranes, as a result of osmotic pressure, may be avoided or reduced. If the osmolarity is suitable, water (plain water, without additional components that could affect osmolarity) may be added to the freeze-dried hydrogel composition to reconstitute the freeze-dried hydrogel composition.

The term "biologics" may be understood, in the context of this specification, to refer to a pharmaceutical product or biological drug manufactured in, extracted from, or semi-synthesized from biological sources. It may include a vaccine, whole blood, blood components, allergenics, somatic cells, material for gene therapy, tissue(s), a recombinant therapeutic protein, and/or living medicines for cell therapy. Biologics may include a sugar, a protein, a nucleic acid, or a combination of these substances. Biologics may, alternatively or additionally, include living cells or tissues. They (or their precursors or components) may be isolated from living sources—e.g. human, animal, plant, fungal, or/or microbial sources.

The biologics may comprise lipids, or they may further comprise lipids. For example, they may comprise a lipid membrane and/or a lipid bilayer.

The biologics may comprise or be e.g. cells, such as spheroids; a tissue or a part thereof; an organoid; a mini-organ; cell components; extracellular vesicles, such as exosomes; virus particles; and/or lipid-based delivery vehicles, such as lipid nanoparticles and/or liposomes.

The cells may be e.g. 3D cell spheroids. However, various types of cells may be cultured in and contained by the hydrogel composition. The cells may be prokaryotic cells, such as bacterial cells, or they may be eukaryotic cells. Eukaryotic cells may be plant cells, yeast cells or animal cells. Examples of eukaryotic cells include transplantable cells, such as stem cells. The cells may be animal cells or human cells. Cells may be cultured cells. Examples of eukaryotic cells include transplantable cells, such as stem cells, for example omnipotent, pluripotent, multipotent, oligopotent or unipotent cells.

Specific examples of cells may include stem cells, undifferentiated cells, precursor cells, as well as fully differentiated cells and/or combinations thereof. Stem cells are undifferentiated or partially differentiated cells, capable of renewing themselves through cell division and can differentiate into multi-lineage cells. These cells may be categorized as embryonic stem cells (ESCs), induced pluripotent stem cells (iPSCs), Hematopoietic stem cells (HSCs), and adult stem cells, also called as tissue-specific or somatic stem cells. In case of human embryonic stem cells, the cells may be from a deposited cell line or made from unfertilized eggs, i.e. "parthenote" eggs or from parthenogenetically activated ovum, so that no human embryos are destroyed. The cells can be maintained and proliferated on or in the hydrogel without animal or human based chemicals originating outside the cells. The cells may be evenly dispersed on or in the hydrogel. Thus, examples of cells include stem cells, undifferentiated cells, precursor cells, as well as fully differentiated cells and combinations thereof. In some examples, the cells comprise cell types selected from the group consisting of keratocytes, keratinocytes, fibroblast cells, epithelial cells and combinations thereof. In some examples the cells are selected from the group consisting of stem cells, progenitor cells, precursor cells, connective tissue cells, epithelial cells, muscle cells, neuronal cells, endothelial cells, fibroblasts, keratinocytes, smooth muscle cells, stromal cells, mesenchymal cells, immune system cells, hematopoietic cells, hepatocytes, dendritic cells, hair follicle cells and combinations thereof. The cells may be tumour or cancer cells, genetically modified cells, such as transgenic cells, cisgenic cells or knock-out cells, or pathogenic cells. Such cells may be used for example for drug research or in therapy. In particular, stem cells may be used in therapeutical applications, for example provided to a patient. However, various other types of cells may also be contemplated.

The tissue may be e.g. a biopsy-type piece of tissue.

Extracellular vesicles (EVs) are vesicles produced by cells which function in various physiological events. They comprise a phospholipid bilayer and may contain various compounds inside the vesicle as cytosol. EVs may include e.g. microvesicles (secreted from the cell membrane, 100-1000 nm in diameter), exosomes (formed from the inner part of the cell, 50-120 nm in diameter), and/or apoptotic bodies (50-5000 nm in diameter, secreted by cells undergoing apoptosis). EVs may differ both in terms of their structure (e.g. surface proteins) and their cargo (e.g. RNAs, proteins, gDNA), depending on their biological task.

Lipid nanoparticles are nanoparticles comprising lipids. The lipid nanoparticles may be spherical. They may have an average diameter of about 10-1000 nm. They may comprise a solid lipid core matrix; such a solid lipid core matrix may be stabilized by an emulsifier.

Liposomes are spherical vesicles having at least one lipid bilayer. Liposomes can be used as a delivery vehicle, e.g. for administration of nutrients and pharmaceutical drugs, such as lipid nanoparticles in mRNA vaccines, and DNA vaccines. Liposomes can be prepared by disrupting biological membranes (such as by sonication). Liposomes may contain phospholipids, especially phosphatidylcholine, but may also include other lipids, such as egg phosphatidylethanolamine. Major types of liposomes may include the multilamellar vesicle (MLV, with several lamellar phase lipid bilayers), the small unilamellar liposome vesicle (SUV, with one lipid bilayer), the large unilamellar vesicle (LUV), the cochleate vesicle, and multivesicular liposomes (in which one vesicle contains one or more smaller vesicles).

Lipid-based delivery vehicles, such as lipid nanoparticles and/or liposomes, or extracellular vesicles, may further comprise other components. For example, they may comprise a protein, such as an antibody; DNA; and/or RNA. Various other components may also be contemplated.

The aqueous solution may comprise or be e.g. at least one of a buffer, saline solution, a cell culture medium, or a mixture or combination thereof. The cell culture medium may be diluted. In this context, the term "diluted" may be considered to refer to cell culture medium that is more dilute than a concentration that is ready to use for culturing cells (which could be considered to be a 1× concentration). The aqueous solution may be biocompatible, i.e. compatible with the biologics.

For example, water may first be added to the freeze-dried hydrogel composition and subsequently an aqueous solution, such as a cell culture medium or a diluted cell culture medium, may be added.

The freeze-dried hydrogel composition may be mechanically agitated, e.g. stirred, upon and/or after adding the water and/or the aqueous solution. However, the mechanical agitation may be relatively gentle. The freeze-dried hydrogel composition may quite readily take up water and/or the aqueous solution and may be reconstituted relatively easily. The reconstitution may thus be relatively gentle to cells.

In embodiments in which the biologics are cells, a tissue or a part thereof, an organoid, a mini-organ, or virus particles, e.g. at least 5% of the cells or of the virus particles may be viable after the reconstitution of the freeze-dried hydrogel composition. Depending on various factors, e.g. at least 10%, or at least 20%, or at least 30%, or at least 40%, or at least 50%, or at least 60%, or at least 70%, or at least 80%, or at least 90% of the cells or of the virus particles may be viable after the reconstitution of the freeze-dried hydrogel composition.

In embodiments in which the biologics are e.g. extracellular vesicles, e.g. at least 5% of the extracellular vesicles may be functional and/or structurally preserved after the reconstitution of the freeze-dried hydrogel composition. Depending on various factors, e.g. at least 10%, or at least 20%, or at least 30%, or at least 40%, or at least 50%, or at least 60%, or at least 70%, or at least 80%, or at least 90% of the extracellular vesicles may be functional and/or structurally preserved after the reconstitution of the freeze-dried hydrogel composition. The functionality of extracellular vesicles may be determined e.g. using a cell viability assay.

The biologics may be collected from the reconstituted hydrogel composition. This may be done, for example, by enzymatically degrading the cellulose nanofibrils and/or cellulose nanocrystals and by collecting the biologics thereby released from the reconstituted hydrogel composition.

The hydrogel composition, the freeze-dried hydrogel composition, and/or the reconstituted hydrogel composition may be provided e.g. in a cell plate format or on another solid support.

A solid support comprising the hydrogel composition, the freeze-dried hydrogel composition, and/or the reconstituted hydrogel composition is therefore also disclosed. The solid support may be e.g. a well plate, such as a 24, 48, 96, 384, or 1536 well plate. The solid support may be e.g. a bag, bottle, column, a syringe or a glass vial, depending on the intended use. Such a solid support may comprise suitable biologics, such as cells, such as spheroids; a tissue or a part thereof; an organoid; a mini-organ; cell components; extracellular vesicles, such as exosomes; and/or virus particles. Such a solid support may be ready to use for cell culture, drug and/or toxicity testing, as a cell model, or other suitable purpose.

Reference will now be made in detail to various embodiments.

The description below discloses some embodiments in such a detail that a person skilled in the art is able to utilize the embodiments based on the disclosure. Not all steps or features of the embodiments are discussed in detail, as many of the steps or features will be obvious for the person skilled in the art based on this specification. Any examples are for illustration purposes only and should not be construed as limiting.

EXAMPLE 1 nNFC (native nanofibrillar cellulose, i.e. native nanofibril cellulose) hydrogels with excipients such as sucrose, and their role to control the amount of residual water in freeze-dried (FDed) nNFC formulations were reconstituted. Formulations used were:
1. 300 mM Trehalose
2. 300 mM Sucrose
3. 150 mM Trehalose+333 mM Glycine
4. Control=1.6% NEC hydrogel The obtained SEM images are presented in FIG. 1.

FIG. 1 shows SEM images of freeze-dried NFC formulation without the excipients (left), with 300 mM of sucrose (left-middle), 300 mM of trehalose (right-middle), 150 mM of trehalose and 333 mM of glycine (right). Zoomed images of the same formulation is presented underneath. Arrows indicate an example of the individual fibrous ribbon observed in the formulations including only trehalose or sucrose. Abbreviations: suc=sucrose, tre=trehalose, gly=glycine.

Figure 2:
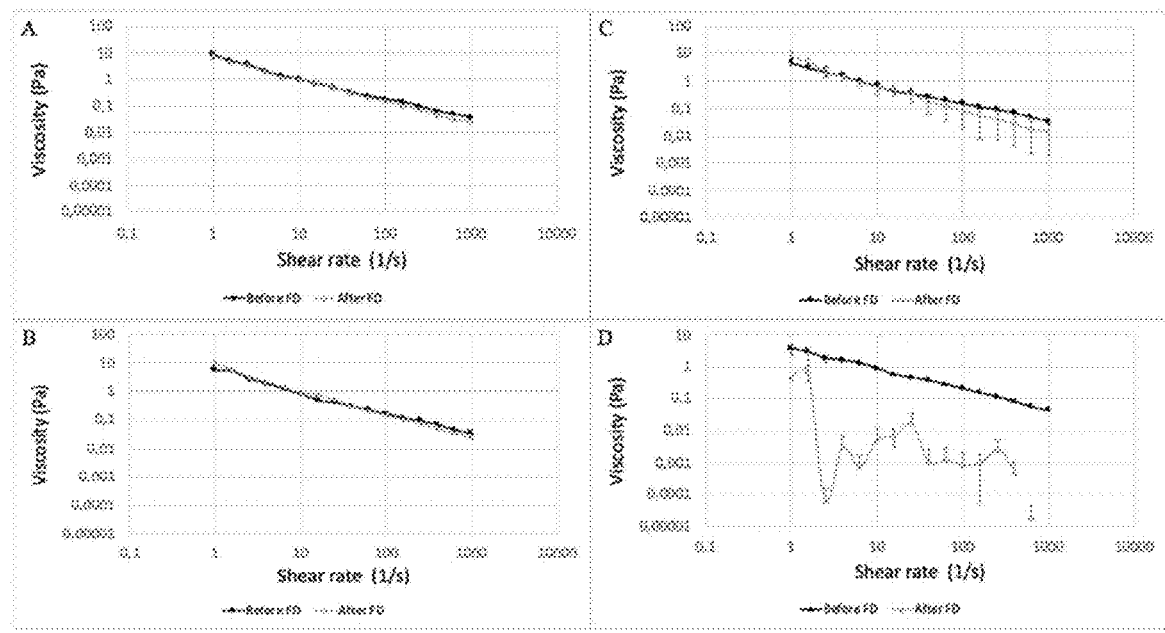
FIG. 2 shows shear rate viscosity before freeze-drying and after the reconstitution of the freeze-dried cake from NFC formulation with 300 mM of sucrose (A),) 150 mM of trehalose and 333 mM of glycine (B), 300 mM of trehalose (B) and with no biomolecules (control, D) (mean±S.D., n=3). Abbreviations: FD=freeze-drying.

The measured viscosities of these formulations are shown in FIG. 2.

FIG. 2 shows shear rate viscosity before freeze-drying and after the reconstitution of the freeze-dried cake from NFC formulation with 300 mM of sucrose (A),) 150 mM of trehalose and 333 mM of glycine (B), 300 mM of trehalose (B) and with no biomolecules (control, D) (mean±S.D., n=3). Abbreviations: FD=freeze-drying.

EXAMPLE 2

Freeze-Drying PC3 and PNT2 Cell Lines Originated EVs for Long-Term Storage in NFC Matrix The formulations used for the FDing of PC3 and PNT2 EVs were:
Form 1: 200 mM Tre (trehalose), 75 mM GLY (glycine), 25 mM HEPES, 0.8% NFC, MQ water
Form 2: 275 mM TRE, 25 mM HEPES, 0.8% NFC, MQ
Form 3: 200 mM SUC, 75 mM GLY, 25 mM HEPES, 0.8% NFC, MQ
Form 4: 275 mM SUC, 25 mM HEPES, 0.8% NFC, MQ
Form 5: 200 mM Tre, 75 mM GLY, 25 mM HEPES, MQ
Form 6: 275 mM TRE, 25 mM HEPES, MQ
Form 7: 200 mM SUC, 75 mM GLY, 25 mM HEPES, MQ
Form 8: 275 mM SUC, 25 mM HEPES, MQ
Form 9: 0.8% NFC+300 mM HEPES
Form 10: 300 mM HEPES The reconstitution of the EVs nNFC hydrogel was first studied. The data obtained is presented in FIG. 3.

Figure 3:
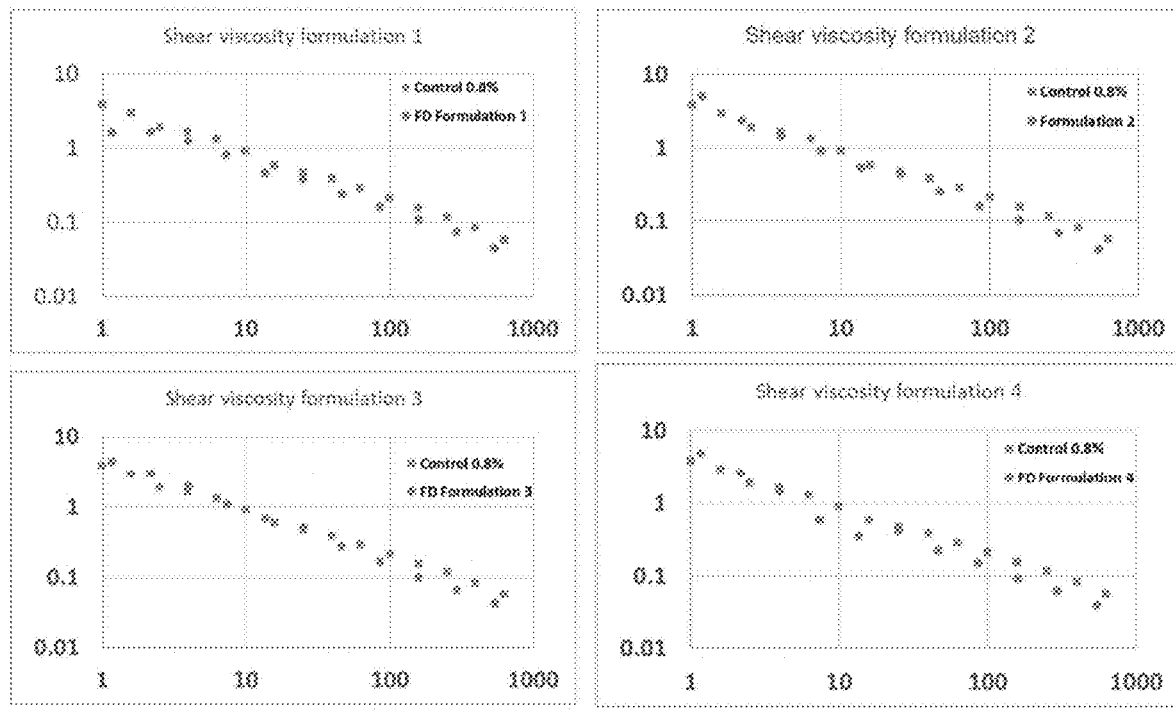
FIG. 3 illustrates the viscosity of the nNFC (native NFC) hydrogel FDed formulations and their reconstitution.

FIG. 3 illustrates the viscosity of the nNFC hydrogel FDed formulations and their reconstitution. Formulations presented are:
Form 1: 200 mM Tre, 75 mM GLY, 25 mM HEPES, 0.8% NFC, MQ;
Form 2: 275 mM TRE, 25 mM HEPES, 0.8% NFC, MQ;
Form 3: 200 mM SUC, 75 mM GLY, 25 mM HEPES, 0.8% NFC, MQ;
Form 4: 275 mM SUC, 25 mM HEPES, 0.8% NFC, MQ The size distribution of the FDed EVs after the enzymatic degradation is presented in FIG. 4.

Figure 4:
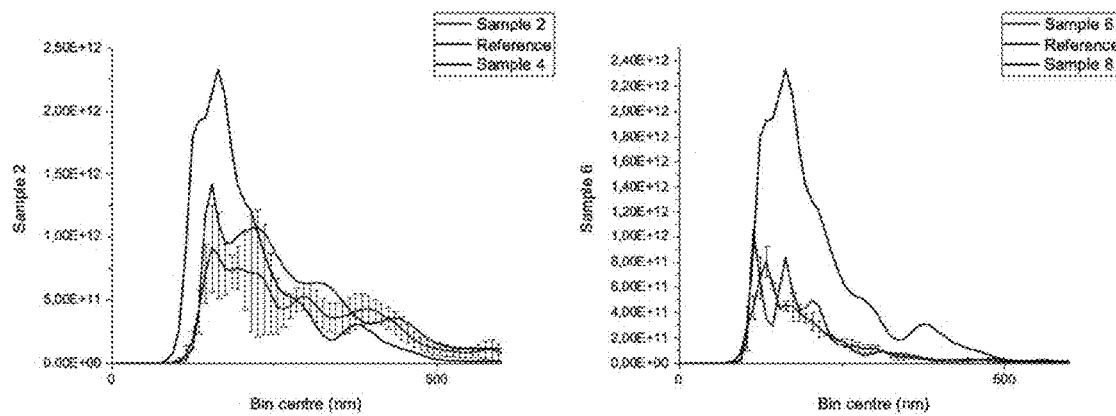
FIG. 4 shows the size distribution of the PC3 cell line originated EVs after the FDing in nNFC hydrogel formulations and enzymatic degradation of nNFC.

FIG. 4 shows the size distribution of the PC3 cell line originated EVs after the FDing in nNFC hydrogel formulations and enzymatic degradation of nNFC. In the graph on the left in FIG. 4, the highest peak depicts the Reference, the middle peak depicts Sample 4, and the lowest peak depicts Sample 2. In the graph on the right in FIG. 4, the highest peak depicts the Reference, the middle peak depicts Sample 8, and the lowest peak depicts Sample 6. The nNFC hydrogel formulations used were:
Form 2: 275 mM TRE, 25 mM HEPES, 0.8% NFC, MQ;
Form 4: 275 mM SUC, 25 mM HEPES, 0.8% NFC, MQ;
Form 6: 275 mM TRE, 25 mM HEPES, MQ;
Form 8: 275 mM SUC, 25 mM HEPES, MQ.
Reference is the used stock PC3 derived EVs without FDing and stored in +4° C.

The amount of the particles after the FDing and reconstitution in nNFC hydrogel formulations and enzymatic degradation of nNFC in presented in FIG. 5.

FIG. 5 shows the amount of the PNT2 cell line derived EVs after the FDing in the nNFC formulations and reconstitution and the enzymatic degradation of nNFC, and the FDing of those EVs without nNFC hydrogel formulations. The formulations used were:

Form 1: 200 mM Tre, 75 mM GLY, 25 mM HEPES, 0.8% NFC, MQ;
Form 2: 275 mM IRE, 25 mM HEPES, 0.8% NFC, MQ;
Form 3: 200 mM SUC, 75 mM GLY, 25 mM HEPES, 0.8% NFC, MQ;
Form 4: 275 mM SUC, 25 mM HEPES, 0.8% NFC, MQ;
Form 5: 200 mM Tre, 75 mM GLY, 25 mM HEPES, MQ;
Form 6: 275 mM TRE, 25 mM HEPES, MQ;
Form 7: 200 mM SUC, 75 mM GLY, 25 mM HEPES, MQ;
Form 8: 275 mM SUC, 25 mM HEPES, MQ;
Form 9: 0.8% NFC+300 mM HEPES;
Form 10: 300 mM HEPES.

Based on the data it appeared that FDing of nNFC formulations with EVs was successful according to residual water contents <1%.

Nanoparticle tracking analyzer (NTA) analysis was performed before freeze-drying and after freeze-drying, reconstitution and enzymatic degradation of nNFC.

NFC matrix with excipients was successfully FDed and the formulations formed solid, white cakes (FIGS. 6A-D). The FDed cakes were successfully reconstituted with MQ-water when correct excipients were used in the formulation. Samples with trehalose or with trehalose and glycine formed the solid white cakes, while samples with DMSO or glycerol collapsed. NFC samples FDed with trehalose formed highly porous, continuous, aerogel structure (FIG. 6E) and when zoomed more closely, the regular fiber structure was found (FIG. 6F). NFC samples FDed without excipients had irregular fiber structure and there were no porous structure present.

Formulations and their residual water contents are presented in Table 1. Residual water contents can be controlled by adjusting the excipient formulation. This may be important when considering the application of FDing of EVs, single cells and 3D cell spheroids, as it is shown in the literature that biological samples may require certain amount of water to be reconstitutable.

TABLE 1

FDed NFC excipient formulations and their residual water contents are mole percent.

| Formulation | Residual water content, mole percent |
| --- | --- |
| 0.8% NFC, 300 mM trehalose, MQ-water | 8.67% |
| 0.8% NFC, 750 mM trehalose, MQ-water | 35.65% |
| 0.8% NFC, 1000 mM trehalose, MQ-water | 47.66% |
| 0.8% NFC, 300 mM sucrose, MQ-water | 5.81% |
| 0.8% NFC, 150 mM trehalose, 150 mM sucrose, MQ-water | 39.53% |
| 0.8% NFC, 300 mM trehalose, 300 mM sucrose, MQ-water | 11.94% |
| 0.8% NFC, 150 mM trehalose, 5% glycine, MQ-water | 13.43% |
| 0.8% NFC, 150 mM trehalose, 666 mM glycine, glycerol 2.5%, MQ-water | 11.60% |
| 0.8% NFC, 150 mM trehalose, 666 mM glycine, DMSO 2.5%, MQ-water | 15.39% |
| 0.8% NFC, MQ-water | 5.62% |

EXAMPLE 3

Modelling of FDed NFC

The interactions between water, excipients and NFC were studied with molecular dynamics (MD) simulations. The MD simulations were run to study the dynamic behaviour of the system and to gain specific mechanistic insights.

The simulation system was investigated to see if the binding strength between sugars and NEC differ, e.g., in the case of monosaccharides when compared with disaccharide systems. It was also investigated whether the introduction of glycine molecules increases the interaction of sugars with NFC surface. The molecules that were simulated with NFC included trehalose, fructose, glucose, lactose, saccharose, and xylitol. All sugar molecules were simulated with an amorphous nanocellulose chain model.

Three plane-like simulation systems were developed: cellulose in a crystalline morphology to determine the binding free energies, one with a hydrophobic surface and one with a hydrophilic surface, and cellulose in an amorphous morphology to determine the biomolecules' effects on water penetration. To the equilibrated water systems excipients were added at random positions of the water phase in concentrations according to the number of water molecules.

Three properties were of particular interest: the free energy difference between the excipients and the cellulose layer, water penetration in amorphous systems and the chain peeling effect of the sugars in crystalline systems noticed during visualization. The free energy differences were determined by producing the potentials of mean force from the partial densities of the excipients via gmx density. The more stable side of the cellulose plane was used to quantify the free energy difference. Water penetration was calculated with the average number of water molecules within 1 nm of a plane along the x- and y-axes formed by the centre of mass of cellulose using gmx select. The average number of glucoses within the same area was determined with the same method, with the exception of using carbon molecules and dividing it by 6. Lastly, gmx rms was used on the eight chains on the top and bottom of both crystalline cellulose layers to determine the RMSD of those individual chains, which gave a metric on the chain peeling as a function of time. The results for the binding of excipients to the surface of NFC were consistent between different cellulose planes.

In all cases, the effect of two different glycine concentrations on surface binding and chain peeling was investigated. Namely, for each sugar three different simulations were carried out with differing sugar concentrations of 300, 225, and 200 mM. In these systems, the concentration of glycine was set to 0, 75, or 100 mM, respectively. Therefore, the total concentration of all excipients was 300 mM in each simulation.

Figure 7:
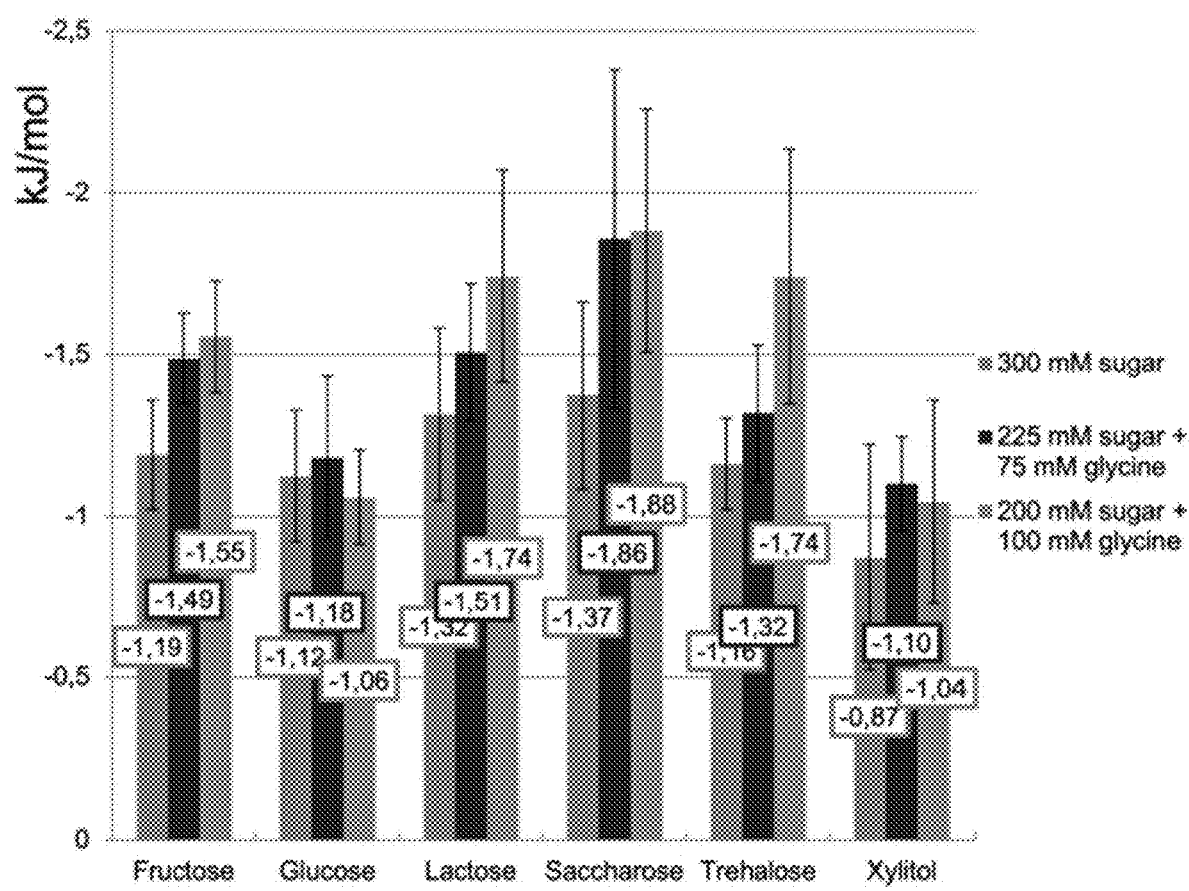
FIG. 7 illustrates binding free-energies for all sugars studied in a molecular modelling system with and without glycine molecules.

The results in FIG. 7 indicate that all sugar molecules have a preference to concentrate on the NFC-water interface. The left column for every saccharide shows the results for 300 mM of saccharide, the column in the middle shows the results of 225 mM of each saccharide combined with 75 mM of glycine, and the right column shows the results for 200 mM of each saccharide combined with 100 mM of glycine. The binding strength, however, differed between the systems. The highest binding free energies were registered for saccharose and lactose (without glycine). Slightly lower surface interactions were seen in the case of fructose, glucose, and xylitol. Clear differences between the systems are difficult to estimate as the resulting standard deviations overlap between sugars. However, the same binding strength trend exists between the systems after the addition of glycine, showing the strongest surface binding for lactose, saccharose, and trehalose. The addition of glycine did not increase the binding strength of glucose. Yet, in all other cases, the addition of glycine increased the binding. Based on the results it seems that glycine-promoted stronger binding is a quite generic outcome. The lowest binding free energy of −0.87 kJ/mol without glycine was acquired for xylitol and the highest for saccharose (−1.37 kJ/mol). If the molar % of xylitol and saccharose at the interface is estimated based on the following equation $\Delta G = RT \ln K_D$ we acquire values of 59 mol % and 64%. This means that at any given time 59-64 mol % of the sugars present in the systems are bound to the NFC surface. When glycine is added into the saccharose system (100 mM), the mol % increases to 68. Thus, although the binding of individual sugars can be easily reversed by thermal energy, it is strong enough to generate a moderately dense sugar layer on the surface of NEC which likely helps to maintain the proper mechanical and morphological properties of NFC after freeze-drying.

There was a strong correlation between the binding free energy of sugars and their complexities. The number of hydrogen bonds (HBs) formed between sugars and the NFC surface was calculated. The number of HBs was the highest for lactose, saccharose, and trehalose, which correlates also with their ability to bind NFC surface hut also with the number of chemical groups that can form hydrogen bonds.

Figure 8A:
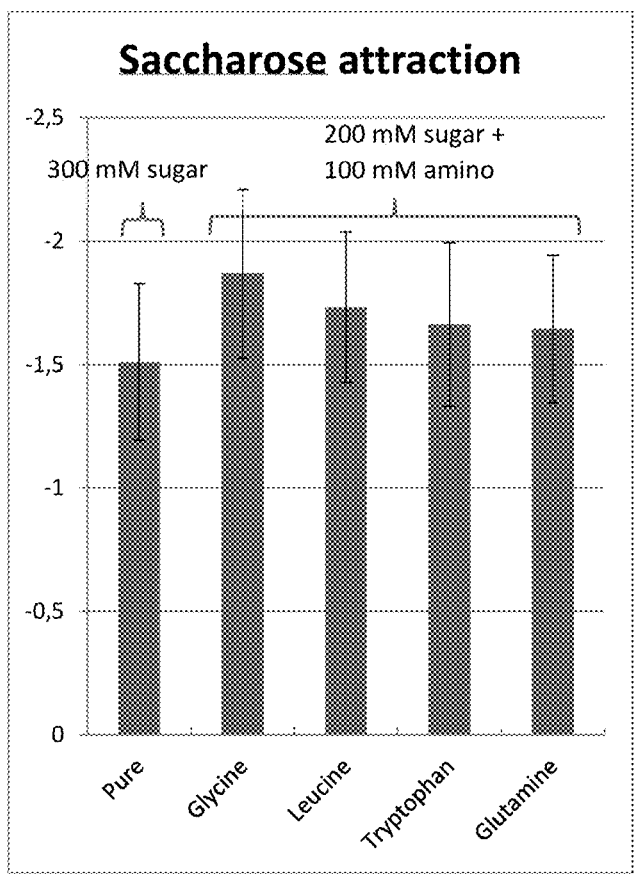
FIG. 8A shows simulation results relating to attractive free energies to cellulose.
Figure 8B:
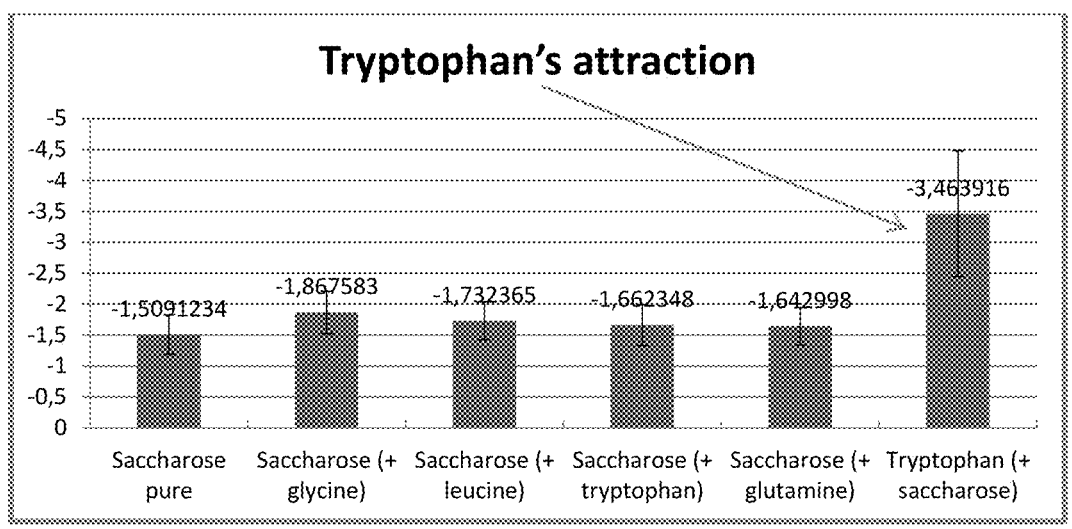
FIG. 8B shows further simulation results relating to attractive free energies to cellulose.

FIGS. 8A and 8B show simulation results relating to attractive free energies to cellulose. Various amino acids tested (glycine, leucine, tryptophan, and glutamine) improved saccharose's attraction to cellulose. FIG. 8B shows the same results as FIG. 8A to compare to tryptophan. Tryptophan had a significantly higher attraction than saccharose.

Figure 9A:
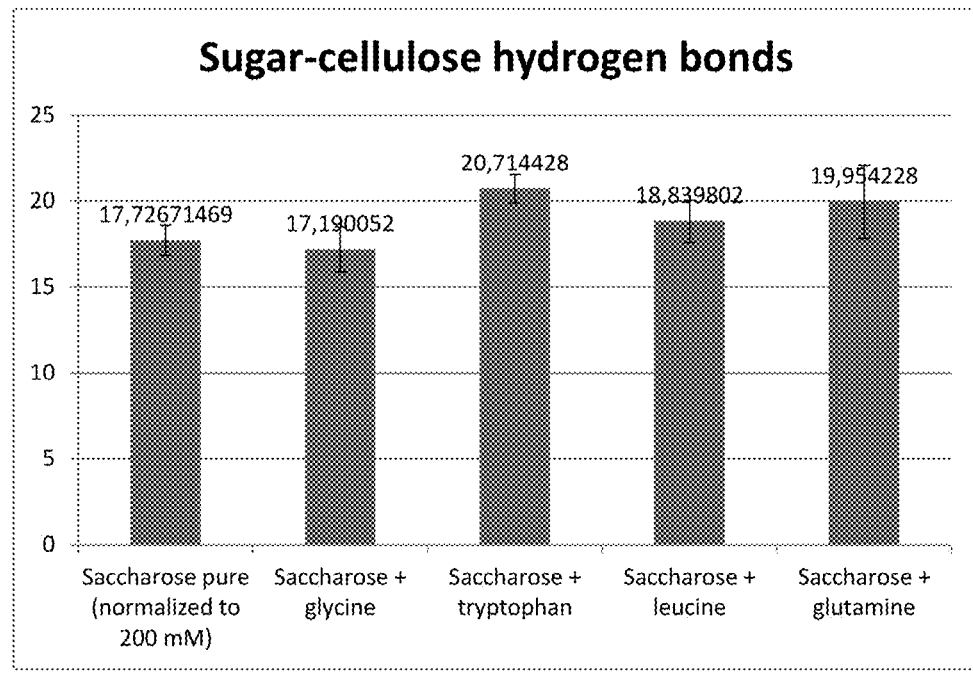
FIG. 9A illustrates that sugar-cellulose hydrogen bonds seemingly increased with amino acids.
Figure 9B:
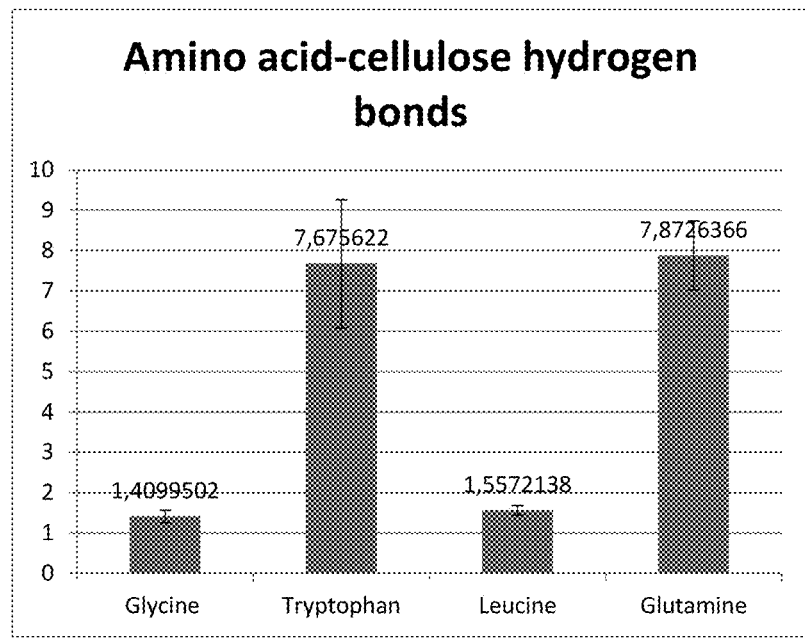
FIG. 9B further illustrates that sugar-cellulose hydrogen bonds seemingly increased with amino acids.

As show in FIGS. 9A and 9B, sugar-cellulose hydrogen bonds seemingly increased with amino acids (although not with glycine). Tryptophan and glutamine shared a high number of hydrogen bonds to cellulose although glutamine was not attracted to cellulose.

EXAMPLE 4

FDing EVs for Long-Term Storage in NFC Matrix

Figure 10:
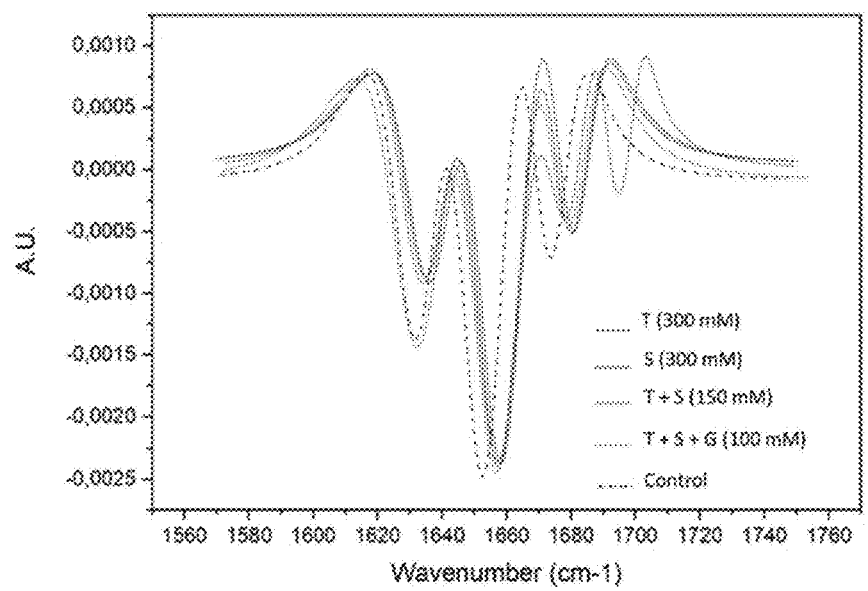
FIG. 10 shows the FTIR spectra of fresh and FDed PC3 derived EVs.

Preliminary results showed that EVs FDed with trehalose, glycine and sucrose were protected from the damage caused by FDing. The FTIR spectra (FIG. 10) shows that there were only minor changes in the protein structure of FDed EVs, when trehalose, sucrose and glycine were used as lyoprotectants.

EXAMPLE 5

FDing 3D Cell Spheroids for Long-Term Storage in NFC Matrix

TABLE 2

Glass transition temperature of maximally freeze-concentrated samples with different formulations with 3D cell spheroids

| Formulation | Tg' |
| --- | --- |
| 0.4% NFC, 150 mM trehalose, 100 mM glycine, MQ | −43.2° C. |
| 0.4% NFC, 200 mM trehalose, 100 mM glycine, | −41.7° C. |

TABLE 2-continued

Glass transition temperature of maximally freeze-concentrated samples with different formulations with 3D cell spheroids

| Formulation | Tg' |
| --- | --- |
| MQ | |
| 0.4% NFC, 300 mM trehalose, 100 mM glycine, MQ | −38.4° C. |
| 0.4% NFC, 150 mM trehalose, 100 mM glycine, 0.5% DMSO, MQ | −50.9° C. |
| 0.4% NFC, 200 mM trehalose, 100 mM glycine, 0.5% DMSO, MQ | −47.3° C. |
| 0.4% NFC, 300 mM trehalose, 100 mM glycine, 0.5% DMSO, MQ | −43.4° C. |
| 0.4% NFC, 200 mM trehalose, 100 mM glycine, 1% DMSO, MQ | −52.3° C. |
| 0.4% NFC, 300 mM trehalose, 100 mM glycine, 1% DMSO, MQ | −47.1° C. |

Figure 11:
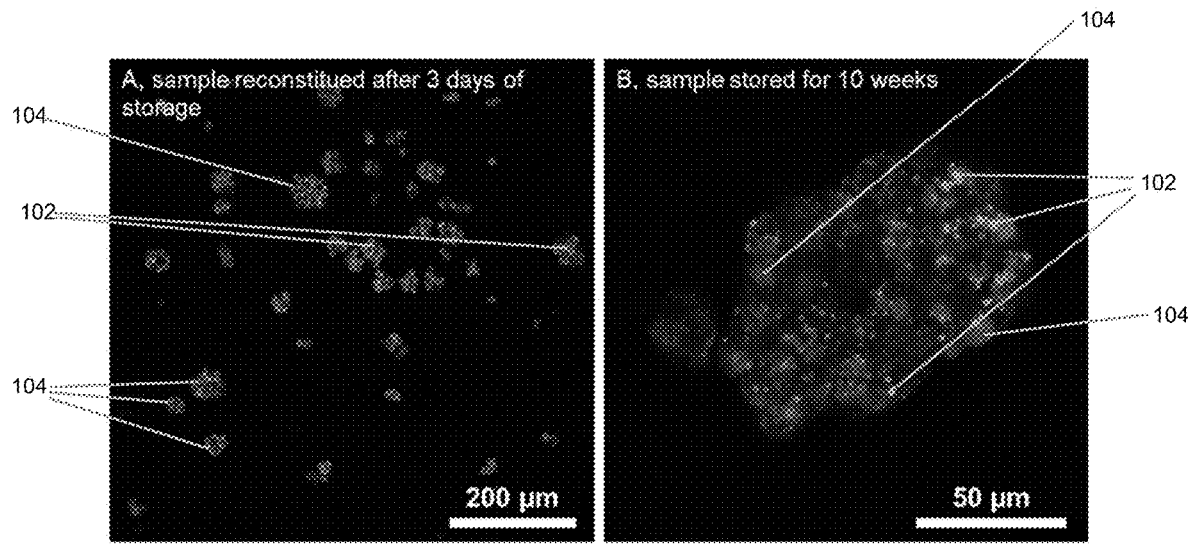
FIG. 11 shows FDed and reconstituted 3D cell spheroids stained with live/dead double staining kit. Enzymatic activity is partly preserved (areas 102), however, the cell membrane is damaged and cells are not fully viable (areas 104).

Thirdly, single cells and 3D cell spheroids were FDed with NFC and excipient formulations and the viability and morphology of the cells was studied. No fully viable cells were recovered, however, enzymatic activity of the FDed 3D cell spheroids was partly preserved (FIG. 11). Furthermore, the 3D structure of FDed cell spheroids was preserved (FIG. 12) and most importantly, the cytoskeleton of the cell spheroids was preserved after FDing and reconstitution (FIG. 13) when trehalose and glycine were used as excipients.

FIG. 11. FDed and reconstituted 3D cell spheroids stained with live/dead double staining kit. Enzymatic activity is partly preserved (areas 102), however, the cell membrane are damaged and cells are not fully viable (areas 104).

Figure 12:
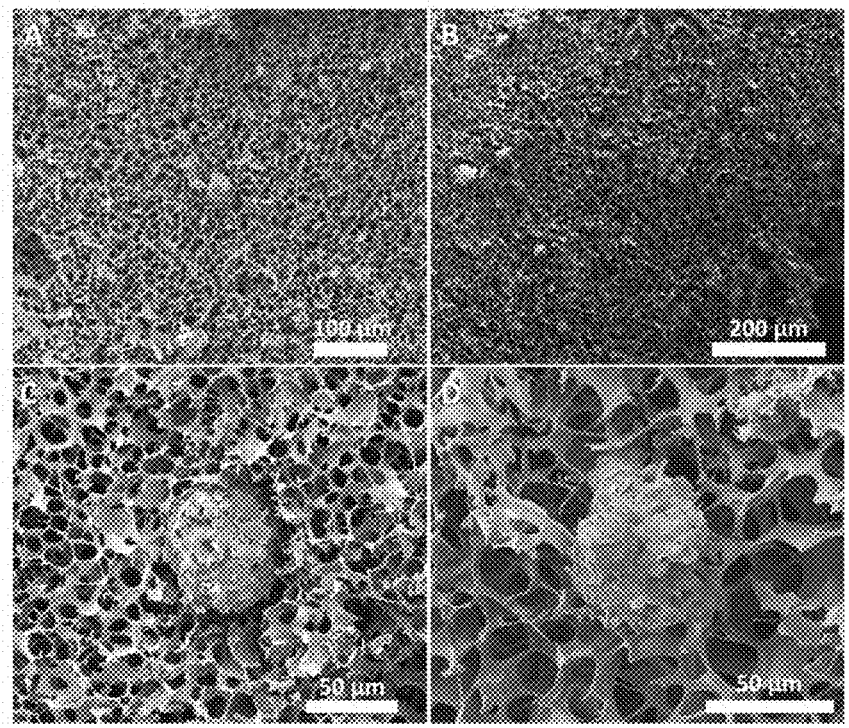
FIG. 12 Scanning electron microscope (SEM) micrographs showing A) & B) regular, porous, structure of FDed NFC aerogel with 3D cell spheroids, C) encapsulated 3D cell spheroid in NFC aerogel with preserved 3D structure and morphology and D) a 3D cell spheroid encapsulated in NFC aerogel with intact cell membrane. Highly porous and interconnected pores in NFC aerogel are clearly visible.

FIG. 12. Scanning electron microscope (SEM) micrographs showing A) & B) regular, porous, structure of FDed NEC aerogel with 3D cell spheroids, C) encapsulated 3D cell spheroid in NFC aerogel with preserved 3D structure and morphology and D) a 3D cell spheroid encapsulated in NFC aerogel with intact cell membrane. Highly porous and interconnected pores in NFC aerogel are clearly visible.

Figure 13:
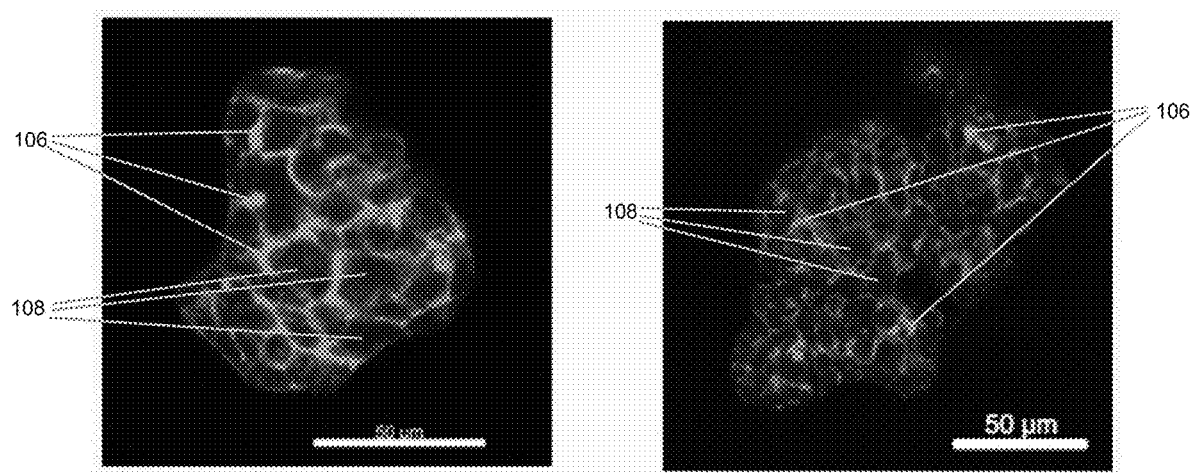
FIG. 13. Cell cytoskeleton, F-actin (areas 106), and nuclei (areas 108) of positive control (left) and FDed and reconstituted 3D cell spheroid (right).

FIG. 13. Cell cytoskeleton, F-actin (areas 106), and nuclei (areas 108) of positive control (left) and FDed and reconstituted 3D cell spheroid (right). The cytoskeleton (F-actin) structure of the FDed cell spheroid was preserved with formulation 1.

EXAMPLE 6

Materials and Methods Used in the Examples

Used Methods

FDing was performed with LyoStar II (SP Scientific)). Glass transition temperatures and melting points were analysed with differential scanning calorimetry (DSC, TA instruments). Osmolarities of NFC formulations were analysed with Osmomat 3000 (Gonotec). Viscosity, loss modulus and storage modulus were studied with Viscometer (Thermo Scientific). Residual water contents were measured with Karl Fischer titrator (Mettler Toledo). The MD simulations were run to study the dynamic behaviour of the system and to gain specific mechanistic insights. Morphology of FDed NFC samples and 3D cell spheroids were analysed with scanning electron microscopy (SEM, FEI Company). Viability of 3D cell spheroids was analysed by staining cells with live/dead double staining kit and analysing samples with confocal microscope (Leica). Cytoskeleton of 3D cell spheroids was studied by staining actin with Phalloidin-Alexa 488 and nuclei with DAPI and imaging 3D cell spheroids with confocal microscope (Leica). Metabolic activity of 3D cell spheroids was evaluated with AlamarBlue assay and with VarioskanLux (Thermo Scientific). Number and concentration of FDed EVs was studied with nanoparticle tracking analysis (NTA, Malvern). Preservation of EV's proteins and protein/lipid ratio was evaluated with FT-IR (Mettler Toledo). Functionality of FDed EVs was studied with a cell viability assay.

EXAMPLE 7

Freeze-Drying Protocol Optimization of the nNFC Hydrogel

The study was started with 26 different NFC formulation and the number was reduced to two with the control before the last rheological measurements based on the results from the former experiments. Tg' temperatures were measured for all 26 formulations and freeze-drying was performed to the ones with the Tg' higher than −50° C. including the control. Cake appearance was analyzed and collapsed ones were eliminated. The formulations with the osmotic pressures before freeze-drying and after the reconstitution higher than 450 mOsmol/kg were discarded. Three formulations were selected for rheological measurements, from which loss modulus and storage modulus analysis were performed for the last two formulations with the most optimal properties and for the control.

PC3 protocol: GrowDex 1.5% was diluted into 1.0% with F-12K media supplemented with 10% FBS and with PC3 cell concentration of 800.000 cells/ml (80.000 cell/well). 100 µl of GrowDex-media-cell suspension was seeded on Low-adhesion well plates and 100 µl of fresh F12K media supplemented with 10% FBS was pipetted on top of the hydrogel mixture. Cells were incubated at 37° C. with 5% $CO_2$.

Figure 14:
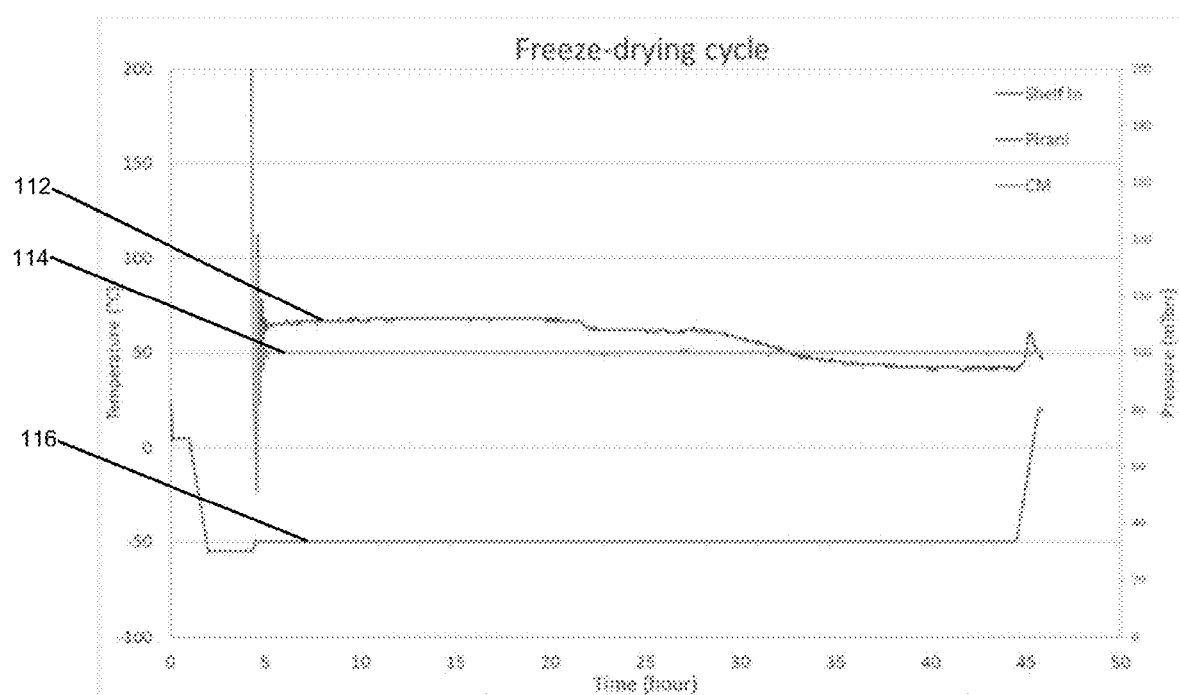
FIG. 14 describes an example of the freeze-drying cycle used with the cells.

Freeze-drying protocol: In the FDing, samples were first frozen by 1° C./minute until −55° C. and they were kept at −55° C. for two hours. Then, the pressure of the FDing chamber was decreased to 100 mTorr and the temperature increased for the EVs to −40° C. and for the NFC matrix and cell samples to −50° C. (Primary drying). After the primary drying, the secondary drying was started. It was performed by increasing the shelf temperature by 1° C./min from −40° C./−50° C. to room temperature. The vials were closed under reduced pressure and with dry nitrogen atmosphere. The FDing cycle lasted for EVs approximately 20 hours and for NEC matrix and cells approximately 48 hours. Example of the FDing cycle is shown in FIG. 14. The upper data points/line 112 represent Pirani, the middle data points/line 114 represent CM, and the lower data points/line 116 represent Shelf In.

It is obvious to a person skilled in the art that with the advancement of technology, the basic idea may be implemented in various ways. The embodiments are thus not limited to the examples described above; instead they may vary within the scope of the claims.

The embodiments described hereinbefore may be used in any combination with each other. Several of the embodiments may be combined together to form a further embodiment. A method, a product, or a use, disclosed herein, may comprise at least one of the embodiments described hereinbefore. It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item refers to one or more of those items. The term "comprising" is used in this specification to mean including the feature(s) or act(s) followed thereafter, without excluding the presence of one or more additional features or acts.

The invention claimed is:

1. A method for freeze-drying a hydrogel composition, the method comprising:
providing the hydrogel composition, wherein the hydrogel composition comprises cellulose nanofibrils and/or cellulose nanocrystals, at least one saccharide, at least one amino acid, and biologics, the content of the at least one saccharide in the hydrogel composition being 100-1000 mM, the content of the at least one amino acid in the hydrogel composition being 50-700 mM, the at least one amino acid comprising glycine, leucine, isoleucine, tryptophan, or any combination thereof, the biologics comprising eukaryotic cells, a tissue, an organoid, a mini-organ, extracellular vesicles, or any combination thereof; and
freeze-drying the hydrogel composition, thereby obtaining a freeze-dried hydrogel composition.

2. The method according to claim 1, wherein the hydrogel composition comprises cell culture medium, the method further comprising removing the cell culture medium from the hydrogel composition at least partially and replacing it with a solution comprising the at least one saccharide and the at least one amino acid prior to freeze-drying the hydrogel composition.

3. The method according to claim 1, wherein the at least one saccharide comprises or is at least one of a disaccharide, a trisaccharide, an oligosaccharide, or a mixture or combination thereof.

4. The method according to claim 1, wherein the at least one saccharide comprises or is at least one of sucrose, trehalose, lactose, or a mixture or combination thereof.

5. The method according to claim 1, wherein the content of the at least one saccharide in the freeze-dried hydrogel composition is in the range of 15-80 mol %.

6. The method according to claim 1, wherein the content of the at least one amino acid in the freeze-dried hydrogel composition is in the range of 15-60 mol %.

7. The method according to claim 1, wherein the ratio of the content of the at least one saccharide and the content of the at least one amino acid in the hydrogel composition and/or in the freeze-dried hydrogel composition is in the range of 10:1-1:5.

8. The method according to claim 1, wherein the residual water content of the freeze-dried hydrogel composition is at most 4 w-%.

9. The method according to claim 1, wherein the at least one amino acid is glycine.

* * * * *